United States Patent [19]

Hirvonen et al.

[11] Patent Number: 5,043,331

[45] Date of Patent: Aug. 27, 1991

[54] TREATMENT OF POSTMENOPAUSAL DISORDERS

[75] Inventors: Erkki Hirvonen, Helsinki; Ariel Gordin, Espoo, both of Finland

[73] Assignee: Orion-yhtyma Oy, Espoo, Finland

[21] Appl. No.: 366,424

[22] Filed: Jun. 15, 1989

[51] Int. Cl.⁵ .............................................. A01N 45/00
[52] U.S. Cl. .................................... 514/170; 514/169
[58] Field of Search ................................ 514/169, 170

[56] References Cited

U.S. PATENT DOCUMENTS 4,425,339 1/1984 Pitchford ............................. 514/170
4,826,831 5/1989 Plunkett et al. ...................... 514/170

FOREIGN PATENT DOCUMENTS 2096462 10/1982 United Kingdom ................ 514/170

Primary Examiner—Frederick E. Waddell
Assistant Examiner—Theodore J. Criares
Attorney, Agent, or Firm—Burgess, Ryan & Wayne

[57] ABSTRACT

A method is provided for the treatment of postmenopausal disorders which comprises administering to a woman in single, oral, daily dose form during an uninterrupted consecutive sequence of 90 days.

(a) a daily, oral, dose in an uninterrupted consecutive sequence for 69 days starting on the first day of a naturally occurring or synthetic estrogenic compound effective in the prevention of climacteric symptoms;

(b) a daily, oral dose in an uninterrupted consecutive sequence from the 70th day to the 83rd day following said first day, of a naturally occurring or synthetic estrogenic compound and a compound having progestational activity effective in preventing the development of endometrial hyperplasia; and optionally (c) a daily, oral dose in an uninterrupted consecutive sequence from the 84th to the 90th day following said first day, of a compound free of estrogen and progestogen.

19 Claims, No Drawings

TREATMENT OF POSTMENOPAUSAL DISORDERS

BACKGROUND OF THE INVENTION (1) Field of the Invention

This invention relates in general to a method for the treatment of postmenopausal disorders. In one aspect, this invention is directed to a method for the treatment of postmenopausal disorders which employs a unique sequence of administering an estrogen such as estradiol valerate and a progestogen such as medroxyprogesterone acetate. In a further aspect, the invention relates to estrogen-progestogen treatment in climacterium wherein the undesirable symptoms are eliminated or markedly reduced.

(2) Description of the Related Art

It has been observed that with the aging population the number of postmenopausal women in the world has been steadily increasing. For example, in Finland where the present invention originated, out of a population of approximately 5,000,000 there are about 500,000 postmenopausal women. Many of these women require postmenopausal hormones. For postmenopausal hormone substitution, estrogens are currently the drugs of choice, because in addition to eliminating the climacteric symptoms they correct the metabolic adverse effects related to estrogen deficiency. Recently, interest has also been shown towards prophylactic treatment of osteoporosis by estrogen substitution.

Prior to the present invention conventional preparations for the treatment of postmenopausal symptoms were administered in one month regimens to mimic the rhythm of the normal menstrual cycle. One such preparation is a sequentially administered estrogen-progestogen preparation developed by Orion Pharmaceutica of Espoo, Finland and sold under the tradename "Divina". This preparation has been found to be particularly effective for the treatment of postmenopausal symptoms. It contains estradiol valerate ($E_2V$) 2 mg and medroxyprogesterone acetate (MPA) 10 mg. MPA was chosen as the preferred progestogen component because it does not decrease the HDL cholesterol level. Since HDL cholesterol evidently has an antiatherosclerotic effect it was assumed that the choice of progestogen is important in long-term use. Apart from that, MPA is well tolerated. In studies Divina has been shown effective and well tolerated by postmenopausal women.

Hirvonen et al disclosed in an article published in the New England Journal of Medicine, Mar. 5, 1981, the effect of different estrogen/progestogen combinations on lipoprotein metabolism in postmenopausal women. This treatment also employs a 1-month regimen.

Although the administration of such preparations as a 1 month cyclic regimen is well known and routinely used, it is also known that a prolonged administration of unopposed estrogens causes hyperplasia of the endometrium, and thus an increased risk of cancer. These negative effects of the estrogen treatment are overcome by administration of progestins, that prevents the development of hyperplasia and eause withdrawal bleeding.

Moreover, many of the patients receiving such preparations find the experience of withdrawal bleedings every four weeks when normal menstruation bleedings have stopped, very undesirable and feel the possible exacerbation of postmenopausal symptoms during the tablet free weeks inconvenient. Such complaints can in due course lead to decreased patient compliance.

It has now been found that estrogen valerate can be administered safely for a three month period as opposed to the usual one month period without causing endometrial hyperplasia and wherein certain other positive effects are obtained as hereinafter indicated. Accordingly, one or more of the following objects can be achieved by the practice of the present invention.

It is an object of the present invention to provide a novel method for the treatment of postmenopausal disorders. Another object of the invention is to provide a method for administering to a woman an estrogen and progestogen compound over a 90 days period in accordance with a prescribed regimen. Another object is to provide a method for administering to a woman estradiol valerate in single, oral daily dose form. A still further object is to provide a method for the administering to a woman medroxyprogesterone acetate in single, oral daily dose form for a specified period which overlaps a certain period during which the estradiol valerate is administered. A further object of this invention is to provide a pharmaceutical kit containing the estrogenic and progesterogenic compounds in successively available unit dose form, including a placebo if desired, for the terminal portion of the treatment period. These and other objects will readily become apparent to those skilled in the art in light of the teachings herein set forth.

SUMMARY OF THE INVENTION

In its broad aspect, the present invention relates to a novel method for the treatment of postmenopausal disorders. The method comprises administering to a woman in single, oral, daily dose form during an uninterrupted consecutive sequence of 90 days, estrogenic and progestogenic compounds in accordance with the following regimen:

(a) a daily, oral dose in an uninterrupted consecutive sequence for 69 days of a naturally occurring or synthetic estrogenic compound effective in the prevention of postmenopausal disorders;

(b) a daily, oral dose in an uninterrupted consecutive sequence from the 70th day to the 83rd day following the first day, of a naturally occurring or synthetic estrogenic compound and a compound having progestational activity effective in preventing development of endometrial hyperplasia; and optionally (c) a daily, oral dose in an uninterrupted consecutive sequence from the 84th day to the 90th day following the first day, of a compound free of estrogen and progestogen.

In another aspect, the invention relates to a pharmaceutical kit which provides a convenient means for making the compound successively available in proper order for treatment.

DETAILED DESCRIPTION OF THE INVENTION

As indicated above, the treatment of postmenopausal symptoms with the commercially available product "Divina" ® was effective and well tolerated by women. However, many women found the withdrawal bleedings every four weeks undesirable and in many instances lead to decrease in patient compliance. In contrast, however, patients using the product of the present invention, hereinafter also referred to as "Combination A", in accordance with the treatment method of the present invention wherein withdrawal bleeding occurs only at three month intervals found the method more desirable, well tolerated and climacteric symptoms alleviated. It has also been noted that "Combination A" does not cause endometrial hyperplasia, the effect on lipoprotein metabolism are favorable and it has a preventive effect on osteoporosis.

As previously indicated the treatment method of the present invention employs an estrogen compound, preferably estradiol valerate, and a progestogen compound, preferably medroxyprogesterone acetate, in the indicated regimen.

Other conventional estrogens may be employed as a suitable component in the postmenopausal regimen of this invention and include in addition to estradiol valerate, natural estrogens such as estrone, estrone sulfate, estrone sulfate piperazine salt and their esters as well as synthetic estrogens.

In practice, it has been found that while medroxyprogesterone acetate is preferred, other progestationally active compounds may be employed. Progesterons which may be employed in the present invention include progesterone and its derivatives such as, for example, megestrol acetate, cyproterone acetate, $\Delta^{15}$ levonorgestrel and dydrogesterone acetate. The preferred progesteron is medroxyprogesterone acetate.

The estrogen and progestogen components are employed in a pharmaceutically acceptable nontoxic carrier. In general the compounds are processed with the customary additives, vehicles and/or flavor ameliorating agents in accordance with generally accepted pharmaceutical practices. For the preferred oral administration, tablets, dragees, capsules, pills, suspensions or solutions have been found to be suitable.

The estrogen compound is employed in a daily dose equal in activity to approximately 2 milligrams of estradiol valerate. The progestogen compound is employed in a daily dose equal in activity to approximately 20 milligrams of medroxyprogesterone acetate. Administration of the compounds is done in accordance with the regimen set forth above.

The final 7 days of the regimen is drug free, i.e., either nothing is taken, or preferably a placebo or other preparation free of estrogen and progestogen is taken for this final period.

In contrast to contraceptive regimens, there is no set day on which treatment is commenced. The only requirement is that the patient is clearly in need of treatment for postmenopausal disorders, i.e., the biological production of estrogen has stopped. The appropriate time to commence treatment can best be determined by the patient in consultation with her physician.

The administration of compounds in combination such as estrogen and progestogen according to a set regimen is not new. For example, estrogen and progestogen compounds had been widely used to control the reproduction cycle in women of child-bearing age. For example, U.S. Pat. No. 3,409,721 which issued on Nov. 5, 1968 discloses and claims a method for administering drugs related to the menstrual cycle of a woman and a system for achieving a prescribed regimen related to the ovarian or menstrual cycle.

During 1976, several patents issued in the United States directed to contraceptive methods which utilize combination-type sequential preparations. For example, in U.S. Pat. No. 3,957,982 a contraception method is disclosed which employs the sequential administration of estrogen and progestogen in increasing amounts over the course of a 21 day regimen followed by 7 days without hormone administration.

More recently, U.S. Pat. No. 4,628,051 issued and discloses a method in which estrogen and progestogen are administered daily in a three phase sequence for 21 days with increasing amounts throughout the three phases.

However, the present invention differs markedly from the prior art in that it is directed to the treatment of postmenopausal disorders and utilizes a 90 day regimen which is not disclosed in nor evident from such patents.

In another embodiment, the present invention relates to a pharmaceutical kit or package in which the daily oral dosages are successively available for sequential administration in the proper order over the 90 day period. As indicated above, it may be advisable to maintain the proper regimen by taking a placebo during the last 7 days so that the patient who has become accustomed to taking a tablet daily, will continue the same routine.

Packaging of the compounds can easily be effected so that the tablets can be taken only in the proper sequence and thus avoid any error in the treatment regimen. For example, the tablets can be packaged in the form of a continuous enclosed strip having individual units or compartments which could be appropriately numbered. For the 70th to 83rd day, the two components can be contained in one tablet, which preferably is identical in appearance and size to the tablet containing only the estrogen component. Other packaging preparations or kits will be evident to those well versed in the packaging of pharmaceutical preparations.

In order to demonstrate the effectiveness of using the preparation of the present invention in accordance with the indicated regimen, and its advantages over the one month sequential estrogen-progestin treatment (Divina), a comparative study was undertaken to evaluate the preparation's efficacy and tolerability. The study was conducted at the Helsinki, Finland University Central Hospital, Menopause Clinic of the Department of Obstetrics and Gynecology.

The materials used in the study were:

Divina: Estrogen tablet: 2mg $E_2V$ (estradiol valerate)
Estrogen-progestin tablet: 2 mg $E_2V$ with 10 mg MPA (medroxyprogesterone acetate).
Combination A: Estrogen tablet: 2 mg $E_2V$
Estrogen-progestin tablet: 2mg $E_2V$ with 20 mg MPA.
The Divina group received 1 estrogen tablet daily for 11 days and then one estrogen-progestin tablet daily for 10 days followed by a 7 day drug free period.
The Combination A group received 1 estrogen tablet daily for 69 days and then one estrogen-progestin tablet daily for 14 days followed by a 7 day drug free period.

The subjects used in the study were 60 postmenopausal women, either on conventional Divina or without any treatment and with clearly elevated S-FSH, low S-$E_2$ levels and last menstruation at least 4 months previously. Hysterectomized or hysterectomized and ovariectomized women were also eligible. Patients already on Divina treatment were required to have one month drug-free period before entering the trial to demonstrate the existence of menopausal symptoms.

60 patients aged 45 to 66 years entered the trial; 30 patients in each group. Age at hysterectomy with bilateral ovariectomy or menopause varied from 34 to 55 years. Only one patient in Combination A group and 4 patients in Divina group had no previous treatment for menopausal symptoms.

Efficacy in control of climacteric symptoms was evaluated by interviewing the patients' subjective experiences of the severity of symptoms on a three graded scale: mild-moderate-severe. Cycle control was evaluated from patients own follow-up recording of day of appearance of withdrawal bleeding or unscheduled bleedings, their intensity and duration and possible pain associated with bleeding. Endometrial biopsies and Pap smears were examined by experienced pathologists at the pathology laboratory of Department of Obstetrics and Gynecology at the same hospital Clinical laboratory results were evaluated by normal values.

The patients underwent medical and gynecological examination before the onset of the study and at 6, 12, 18 and 24 months. Clinical laboratory samples (S-$E_2$, S-FSH, S-CHOL (total), S-HDL-CHOL, S-Trigly) and bone mineral density (BMD) determinations were made at the same points. Endometrial biopsies and Pap smears were obtained at the beginning and at 6, 12 and 24 months The patients were interviewed by the study nurse at the onset of the trial and every three months throughout the study.

During the first year:
Divina group: 8 patients discontinued the study; 4 did not continue the second study year.
Combination A group: 1 patient discontinued the study; 3 did not continue the second study year.
During the second year:
Divina group: 1 patient discontinued the study.
Combination A group: 1 patient discontinued the study.

Significant alleviation of the menopausal symptoms was achieved after the first month of treatment with both medications. The percentage of patients reporting hot flushes decreased from 88 to 41% (Divina) and from 88 to 48 (Combination A) corresponding figures for night-time sweating were: 82 41% and 92 40%. The mean S-$E_2$ levels increased from 110 through 292 to 360 pmol/l with Divina and from 102 through 268 to 302 pmol/l in Combination A group (0 12 24 months). The withdrawal bleedings began on cycle day 22.8+2.6 (Divina) and on day 86.2+2.0 (Combination A). The duration of the bleeding was not statistically different between the groups. 5 patients reported heavy bleeding at the first bleeding episode with Combination A and four patients experienced pain as well. Unscheduled bleedings occurred in 1 Divina patient (discontinued) and in 8 Combination A patients (2 discontinued) during the 24 months. Effects on lipid metabolism were favorable with both treatments, the decrease in the mean total S-CHOL levels was about 9% in both groups, S-HDL-CHOL and S-Trigly levels were not affected. No significant changes could be observed in the mean bone mineral densities during treatment in either group.

Endometrial samples did not reveal any hyperplastic or malignant changes. Mild or moderate tenderness and swelling of the breasts was reported by 7/30 (23%) Divina patients and by 13/30 (43%) Combination A patients. In addition 2 Combination A patients experienced severe tenderness of the breasts. These evnts did not cause any discontinuations. Other side effects such as nausea, fatigue and swelling were sporadic and usually mild.

The following tables and discussion provide in more detail summary of the results set forth above and further demonstrate the benefit of the treatment regimen of the present invention.

A. Control of menopausal symptoms

Hot flushes and sweating may be justified as cardinal climacteric symptoms. In this study 82 to 92% of all patients reported these inconvenient symptoms before the start of treatment. In both groups the hormone replacement dramatically reduced both the severity and incidence of all climacteric symptoms. Results obtained are tabulated in Table I:

TABLE I

ALLEVIATION OF CLIMACTERIC SYMPTOMS DURING TREATMENT
Numbers of patients reporting any grade of climacteric symptoms (mild-moderate-severe);
Divina: n = 17, Combination A: n = 25

| Divina Time, months | Hot flushes | Night sweats | Anxiety/tension | Sleep disturbance |
|---|---|---|---|---|
| 0 | 15 (88%) | 14 (82%) | 10 (59%) | 9 (53%) |
| ↓ | ↓* | ↓* | ↓ | ↓ |
| 1 | 7 (41%) | 7 (41%) | 3 (18%) | 5 (29%) |
| ↓ | ↓ | ↓ | ↓ | ↓ |
| 3 | 4 (24%) | 3 (18%) | 2 (12%) | 3 (18%) |
| ↓ | ↓ | ↓ | ↓ | ↓ |
| 12 | 1 (6%) | 3 (18%) | 1 (6%) | 4 (24%) |
| ↓ | ↓ | ↓ | ↓ | ↓ |
| 24 | 1 (6%) | 3 (18%) | 1 (6%) | 1 (6%) |
| Combination A | | | | |
| 0 | 22 (88%) | 23 (92%) | 18 (72%) | 19 (76%) |
| ↓ | ↓* | ↓* | ↓ | ↓ |
| 1 | 12 (48%) | 10 (40%) | 9 (36%) | 11 (44%) |
| ↓ | ↓ | ↓ | ↓ | ↓ |
| 3 | 2 (8%) | 6 (24%) | 6 (24%) | 10 (40%) |
| ↓ | ↓ | ↓ | ↓ | ↓ |
| 12 | 1 (4%) | 3 (12%) | 2 (8%) | 4 (16%) |
| ↓ | ↓ | ↓ | ↓ | ↓ |
| 24 | 3 (12%) | 7 (28%) | 1 (4%) | 4 (16%) |

*Significant decrease from 0 to 1 month p < 0.01.

A significant alleviation was achieved after the first month of treatment (p<0.01) on both medications. After 1 year only 1 (6%) Divina-patient reported hot flushes and 3 (18%) night-time sweating. Similarly, in Combination A group, only 1 patient (4%) complained of hot flushes and 3 patients (12%) of night-time sweating at twelve months.

B. Changes in hormone levels

Serum estradiol values increased as shown in Table II and the serum follicle stimulating hormone values decreased as shown in Table III statistically significantly in both groups during the treatment in comparison to pretreatment values.

TABLE II

| SERUM ESTRADIOL CONCENTRATIONS, pmol/l | | |
|---|---|---|
| Month | Divina | Combination A |
| 0 | 110 | 102 |
| ↓ 0 → 12 p < 0.01 | ↓ | ↓ 0 → 12 p < 0.001 |
| 12 | 292 | 286 |
| ↓ 0 → 24 p < 0.01 | ↓ | ↓ 0 → 24 p < 0.01 |
| 24 | 360 | 302 |

TABLE III

| SERUM FOLLICLE STIMULATING HORMONE (FSH) LEVELS, IU/l | | |
|---|---|---|
| Month | Divina | Combination A |
| 0 | 66 | 66 |
| ↓ 0 → 12 p < 0.001 | ↓ | ↓ 0 → 12 p < 0.001 |
| 12 | 31 | 24 |
| ↓ 0 → 24 p < 0.001 | ↓ | ↓ 0 → 24 p < 0.001 |
| 24 | 25 | 22 |

C. Bleeding pattern and cycle control

Out of the 25 patients in Combination A group who completed two years of treatment, two were previously hysterectomized. In the Divina group, 17 patients completed 24 months, one was hysterectomized. Withdrawal bleedings occurred in both groups.

In Combination A group the bleedings appeared on cycle day 86.2+2.0 (mean +SD; minimum 80th and maximum 92nd day of the cycle). In this group the withdrawal bleeding started on the tablet-free week in 189 out of 201 cycles and 11 times (5%) earlier than scheduled. The latter occurred in five patients and was a constant finding only in one patient, the other four had only sporadic episodes Furthermore, in one patient the bleeding started on the first or second day of the next treatment cycle.

In the Divina group, the withdrawal bleeding started between days 17 to 28 of the cycle, the mean starting day being 22.8+2.6 (mean+SD).

The mean duration of withdrawal bleedings varied between 4 and 5 days with no statistically significant differences between the treatment groups. Heavy bleeding was encountered in five patients of the Combination A at the beginning of the treatment ($p<0.05$). Two patients continued to have heavy withdrawal bleedings throughout the whole study period.

During the first withdrawal bleeding episode at 3 months four Combination A patients experienced intense pain. Later such experiences were not reported, and otherwise no differences could be detected between the treatment groups.

During the first year one Divina patient (24) had unscheduled (intermenstrual) bleedings, which also caused her discontinuation at 5 months. During the second year, no unscheduled bleedings occurred in this group. In Combination A group five patients had unscheduled bleedings during the first year, and five patients during the second year, one of whom had reported unscheduled bleedings already during the first twelve months.

All taken together, during the 24 months' treatment period, unscheduled bleedings occurred in 9 out of the 28 non-hysterectomized patients in Combination A group. This makes up a rather high percentage of 32%, but on the other hand in five patients (18%) the unscheduled bleeding was only scanty (or merely spotting) with a duration of one to four days. Unscheduled bleeding was the reason for discontinuation in only two (7%) Combination A patients.

D. Effects on endometrial histology

Endometrial biopsies were obtained at 6 months in 20 patients of the Combination A group: in five patients the sample was insufficient, one sample displayed atrophy, eleven samples secretory changes (progestin effect) and three samples proliferative stage (estrogen effect only). The findings in the Divina group were: nine secretory stages, three proliferative stags and no atrophic specimens.

At 12 months, samples could not be obtained in three of the non-hysterectomized patients in the Combination A group and in six patients in the Divina group; in Combination A group, one sample was insufficient. Thus, of the 19 evaluable samples in the Combination A patients, one was in proliferative stage, 17 (89%) in secretory stage and one sample showed atrophy. Of the ten samples in the divina group, one was in proliferative stage and 9 (90%) in secretory stage.

At 24 months the histological picture remained essentially the same, with majority of the samples exhibiting secretory phase and only a few samples (one to three) showing proliferative stage or atrophy.

The most important finding in endometrial histology was that no changes indicating hyperplasia or malignancy were observed during the whole 24 months of treatment. Similarly, no indications of malignant changes were observed in the cytological samples (Pap smears) of either group.

E. Effects on lipid metabolism Significant decreases in serum total cholesterol concentrations were observed in both treatment groups at 12 and months. The mean values of total S-CHOL decreased by 9% in both groups (0 24 months) (Table IV). The serum HDL-cholesterol values remained unchanged (Table V). No changes occurred in the triglyceride values either (Table VI).

TABLE IV

| SERUM TOTAL CHOLESTEROL LEVELS, mmol/l | | |
|---|---|---|
| Month | Divina | Combination A |
| 0 | 6.6 | 6.9 |
| ↓ 0 → 12 $p<0.01$ | ↓ | ↓ 0 → 12 $p<0.05$ |
| 12 | 6.2 | 6.8 |
| ↓ 0 → 24 $p<0.057$ | ↓ | ↓ 0 → 24 $p<0.001$ |
| 24 | 6.0 | 6.3 |

TABLE V

| SERUM HDL-CHOLESTEROL LEVELS, mmol/l | | |
|---|---|---|
| Month | Divina | Combination A |
| 0 | 2.1 | 1.7 |
| ↓ | ↓ | ↓ 0 → 0 → 12 NS |
| 12 | 2.0 | 1.7 |
| ↓ | ↓ | ↓ 0 → 24 NS |
| 24 | 2.3 | 1.6 |

TABLE VI

| FASTING SERUM TRIGLYCERIDE LEVELS, mmol/l | | |
|---|---|---|
| Month | Divina | Combination A |
| 0 | 1.2 | 1.3 |
| ↓ | ↓ | ↓ 0 → 12 NS |
| 12 | 1.2 | 1.2 |
| ↓ | ↓ | ↓ 0 → 24 NS |
| 24 | 1.1 | 1.3 |

F. Effects on bone mineral density

Bone mineral density (BMD) is a correlate in which $BMC_2$ values are divided by the bone width of the actual measurement site. It is therefore considered more accurate in follow-up evaluations. The mean BMD values were retained at essentially the same levels during the 24 months of treatment (Table VII). The mean percentual change of BMD was positive at 12 months in both groups; at 24 months it measured—1.0% in Divina group and +1.4% in Combination A patients (Table VIII).

Comparison of the percentual changes in BMD values did not reveal any significant differences between the groups.

TABLE VII

| MEAN BMD VALUES | | |
|---|---|---|
| Month | Divina | Combination A |
| 0 | 1.43 | 1.41 |
| ↓ | ↓ | ↓ 0 → 12 NS |
| 12 | 1.42 | 1.41 |
| ↓ | ↓ | ↓ 0 → 24 NS |
| 24 | 1.40 | 1.43 |

TABLE VIII

| MEAN PERCENTUAL CHANGE IN BMD VALUES | | |
|---|---|---|
| Interval | Divina | Combination A |
| 0 → 12 NS | +0.5% (n = 13) | +0.2% (n = 19) |
| 0 → 24 NS | −1.0% (n = 14) | +1.4% (n = 21) |

It was clearly evident from the comparative study that Combination A is clinically well tolerated and accepted, does not cause endometrial hyperplasia, and the effects on lipoprotein metabolism are favorable. Better compliance and tolerance were demonstrated by fewer discontinuations than with comparison. Combination A was thus shown to be an effective treatment for menopausal symptoms, its safety and its beneficial effects on lipid metabolism were confirmed. An inhibition of postmenopausal osteoporosis was achieved with both treatments as evaluated by BMD values.

Although the invention has been illustrated by the preceding examples, it is not to be construed as being limited to the materials employed therein, but rather, the invention is directed to the generic area as hereinbefore disclosed. Various modifications and embodiments thereof can be made without departing from the spirit or scope thereof.

We claim:

1. A method for the treatment of postmenopausal disorders which comprises administering to a woman in single, oral, daily dose form during an uninterrupted consecutive sequence of 90 days, and in accordance with the following regimen:
   (a) a daily, oral dose in an uninterrupted consecutive sequence of 69 days of a naturally occurring or synthetic estrogenic compound effective in the prevention of postmenopausal disorders in dosage equal in estrogenic activity to approximately 2 milligrams of estradiol valerate;
   (b) a daily, oral dose in an uninterrupted consecutive sequence from the 70th day to the 83rd day following said first day, of a naturally occurring or synthetic estrogenic compound in dosage equal in estrogenic activity to approximately 2 milligrams of estradiol valerate and a compound having progestational activity effective in preventing the development of endometrial hyperplasia in dosage equal in progestogenic activity to approximately 20 milligrams of medroxyprogesterone acetate; and
   (c) a daily, oral dose in uninterrupted consecutive sequence from the 84th to the 90th day following said first day of a compound free of estrogen and progestogen.

2. The method of claim 1 wherein said estrogenic compound is selected from the group consisting of estradiol valerate, natural estrogens and synthetic estrogens.

3. The method of claim 1 wherein said progestogen compound is selected from the group consisting of medroxyprogesterone acetate, megestrol acetate, cyproterone acetate, $\Delta^{15}$ levonorgestrel, and dydrogesterone acetate.

4. The method of claim 2 wherein said estrogenic compound is estradiol valerate.

5. The method of claim 3 wherein said progestogen compound is medroxyprogesterone acetate.

6. The method of claim 1 wherein no compound is administered from said 84th day to said 90th day following said first day.

7. The method of claim 1 wherein said compound free of estrogen and progestogen is a placebo.

8. The method of claim 1 wherein all of said compounds are in tablet form.

9. A pharmaceutical kit in unit dose form for use in the treatment of postmenopausal disorders comprised of 90 separate dosage units for uninterrupted sequential daily, oral administration, said kit comprised of:
   (a) 69 separate daily dosage units for sequential daily, oral ingestion of a naturally occurring or synthetic estrogenic compound effective in the prevention of postmenopausal disorders in dosage equal in estrogenic activity to approximately 2 milligrams of estradiol valerate;
   (b) 14 separate daily dose units for sequential daily, oral ingestion of a naturally occurring or synthetic estrogenic compound in dosage equal in estrogenic activity to approximately 2 milligrams of estradiol valerate and a progesterone compound having a progestational activity effective in preventing the development of endometrial hyperplasia in dosage equal in progestogenic activity to approximately 20 milligrams of medroxyprogesterone acetate; and
   (c) 6-8 separate daily dosage units for sequential daily, oral ingestion of a compound free of estrogen and progestogen.

10. The pharmaceutical kit of claim 9 wherein said estrogenic compound is selected from the group consisting of estradiol valerate, natural estrogens and synthetic estrogens.

11. The pharmaceutical kit of claim 9 wherein said progestogen compound is selected from the group consisting of medroxyprogesterone acetate, megestrol acetate, cyproterone acetate, $\Delta^{15}$ levonorgestrel, and dydrogesterone acetate.

12. The pharmaceutical kit of claim 10 wherein said estrogenic compound is estradiol valerate.

13. The pharmaceutical kit of claim 11 wherein said progestogen compound is medroxyprogesterone acetate.

14. The pharmaceutical kit of claim 9 wherein said compound free of estrogen and progestogen is a placebo.

15. The pharmaceutical kit of claim 9 wherein all of said compounds are in tablet form.

16. The pharmaceutical kit of claim 9 wherein said estrogenic and progesterone compounds are contained in a single tablet.

17. The pharmaceutical kit of claim 9 wherein the unit dosages of (a), (b) and (c) are of uniform size and appearance.

18. The method of claim 1 for the prophylactic treatment of postmenopausal osteoporosis.

19. The pharmaceutical kit of claim 9 for use in the prophylactic treatment of postmenopausal osteoporosis.

* * * * *